United States Patent
Ringler et al.

(10) Patent No.: US 6,878,146 B2
(45) Date of Patent: Apr. 12, 2005

(54) APPARATUS FOR TREATMENT AND PREVENTION OF ALOPECIA

(75) Inventors: Steven L. Ringler, Grand Rapids, MI (US); John K. Biener, Rockford, MI (US)

(73) Assignee: GR Originals, L.L.C., Grand Rapids, MI (US)

( * ) Notice: Subject to any disclaimer, the term of this patent is extended or adjusted under 35 U.S.C. 154(b) by 0 days.

(21) Appl. No.: 10/099,886

(22) Filed: Mar. 15, 2002

(65) Prior Publication Data

US 2002/0151881 A1 Oct. 17, 2002

Related U.S. Application Data

(60) Provisional application No. 60/276,591, filed on Mar. 16, 2001.

(51) Int. Cl.$^7$ ............................................. A61B 18/08
(52) U.S. Cl. .......................................... 606/27; 132/229
(58) Field of Search .............................. 606/27, 28, 31; 607/108–110; 132/118, 229

(56) References Cited

U.S. PATENT DOCUMENTS

| | | | | |
|---|---|---|---|---|
| 4,721,121 A | * | 1/1988 | Adams | 132/212 |
| 5,269,781 A | * | 12/1993 | Hewell, III | 606/45 |
| 5,300,069 A | * | 4/1994 | Hunsberger et al. | 606/37 |
| 5,354,967 A | * | 10/1994 | Barzilai et al. | 219/225 |
| 5,496,314 A | * | 3/1996 | Eggers | 606/41 |
| 6,001,077 A | * | 12/1999 | Ellman et al. | 604/35 |
| 6,053,180 A | * | 4/2000 | Kwan | 132/232 |
| 6,100,501 A | * | 8/2000 | von der Heyde | 219/229 |
| 6,423,942 B1 | * | 7/2002 | Liao | 219/222 |
| 6,569,159 B1 | * | 5/2003 | Edwards et al. | 606/41 |
| 6,572,639 B1 | * | 6/2003 | Ingle et al. | 607/104 |

* cited by examiner

*Primary Examiner*—Roy D. Gibson
*Assistant Examiner*—Aaron Roane
(74) *Attorney, Agent, or Firm*—Price, Heneveld, Cooper, DeWitt & Litton, LLP

(57) ABSTRACT

A heat sealing instrument for use in the treatment and prevention of hair loss and stimulation of new hair includes a heating element, a protective shroud, a handle, and control circuitry. The heating element is heated to a temperature of from about 400 to about 1,000° F. sufficient for fusing and sealing the cuticle, cortex, and medulla layers of a hair shaft. The instrument includes a control panel for monitoring and adjusting the temperature of the heating device and a vacuum source and filter combination for drawing in and filtering the fumes from the area around the heating element.

25 Claims, 4 Drawing Sheets

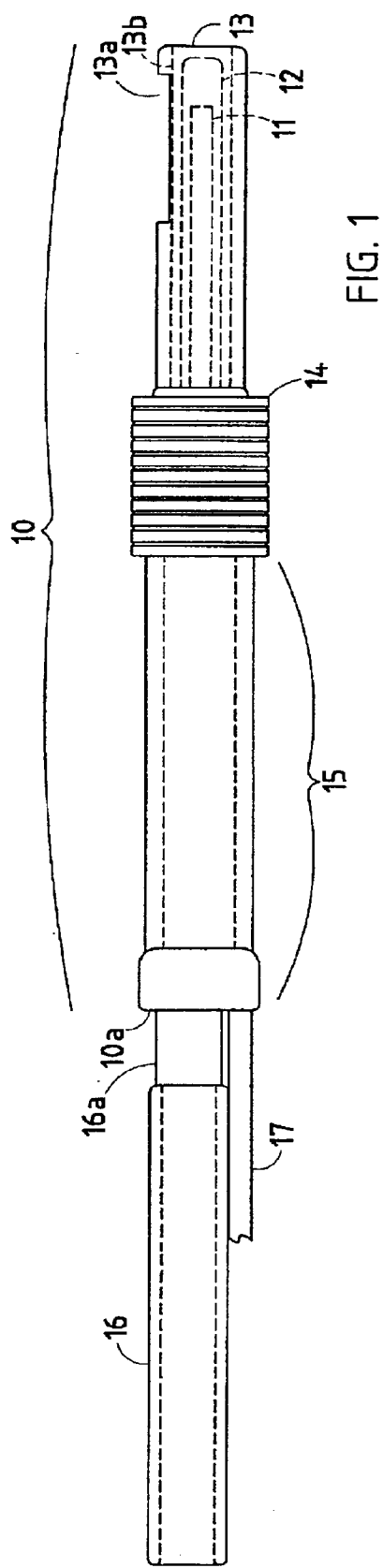
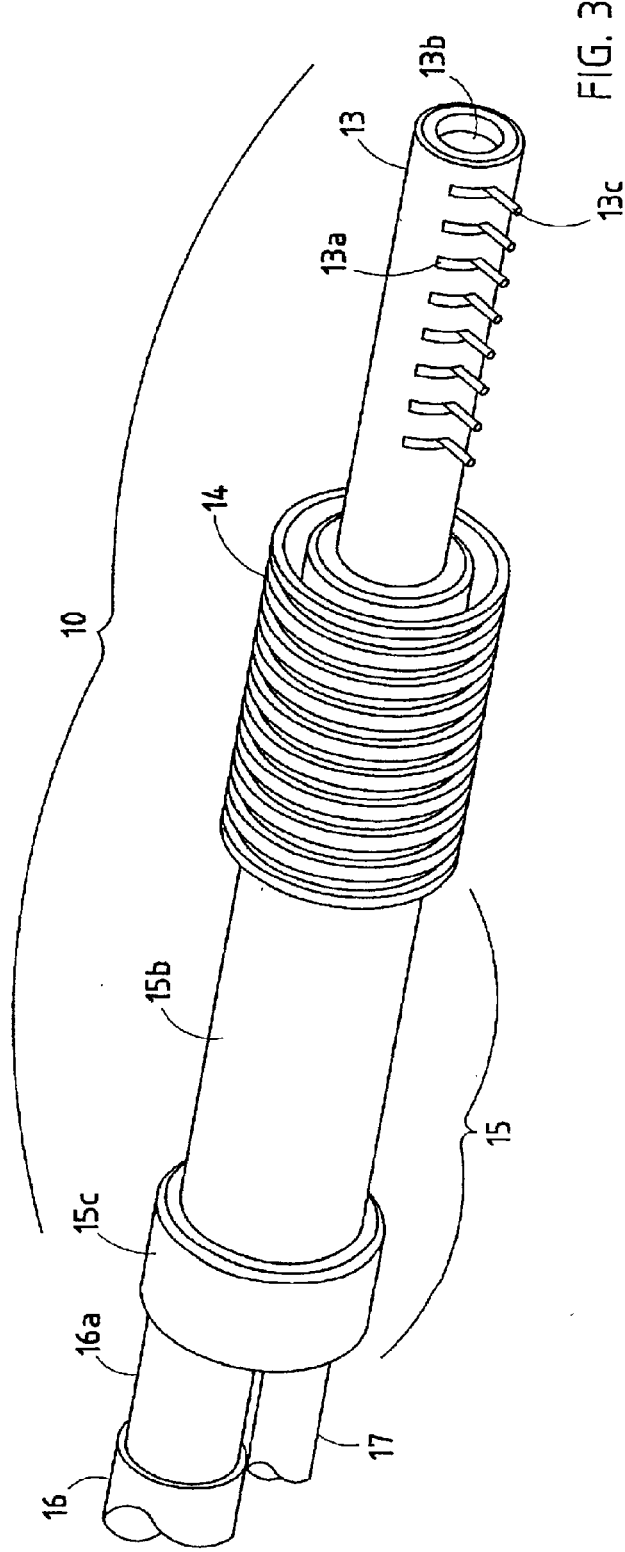
FIG. 1
FIG. 3

APPARATUS FOR TREATMENT AND PREVENTION OF ALOPECIA

This application claims the benefit of U.S. Provisional Patent Application Ser. No. 60/276,591 entitled, "APPARATUS FOR TREATMENT AND PREVENTION OF ALOPECIA", by Steven L. Ringler et al., filed Mar. 16, 2001, the entire disclosure of which is hereby incorporated herein by reference.

FIELD OF THE INVENTION

The present invention relates generally to the treatment and prevention of human or animal alopecia conditions and more specifically to an apparatus for use in treatment of the same.

BACKGROUND OF THE INVENTION

It is estimated that 35 million Americans experience some degree of alopecia, or hair loss, resulting in 900 million dollars a year being spent in efforts to grow it back. Generally, it affects about 30 million men and 20 million women in the U.S. each year. It is believed that baldness is hereditary and occurs when the hair follicles slowly begin to produce finer and shorter hairs, or stop producing hairs at all. There are many forms of hair loss, ranging from alopecia areata to androgenic alopecia, also known as male or female pattern baldness.

Around 40% of men will have some hair loss by their mid 30's, and nearly 60% of women experience some thinning of the hair after menopause. By age 50, half of all males generally experience hair loss patterns as compared to 50–70% of post-menopausal women. Alopecia becomes more common as age increases, but hair loss may start at younger ages. Without drug therapy or cosmetic treatments, alopecia can remain as a permanent condition.

In addition, animals can also suffer from a variety of dermatologic conditions. Such conditions frequently cause stress to the animal's haircoat resulting in hair loss, which further exacerbates an increased health risk to the animal and increased concern to the pet owner. Common examples of dermatologic conditions of animals, which can result in hair loss, include sebaceous adenitis, primary seborrhea, primary idiopathic seborrhea, seasonal alopecia, and other miscellaneous dermatoses.

To treat human alopecia, the prior art has produced an enormous variety of drug and cosmetic treatments. The reason for such a volume of treatment options stems from the difficulty the medical and scientific community have had in establishing the cause of alopecia. Alopecia has many possible causes, such as genetic disorders, infections, contact with toxic agents, and hormone imbalance. Currently, there are only two drugs approved by the Food and Drug Administration to treat alopecia.

Rogaine®, also known as minoxidil, was originally developed as a treatment for individuals with high blood pressure. While treating those individuals, it was discovered that minoxidil also moderately increased hair growth and prevented future hair loss. It is believed that minoxidil may increase hair growth in thinning hair areas. However, there are problems associated with the use of minoxidil. The most common problems are irritation of the skin, and if the medication is stopped after prolonged use, hair loss may actually increase rather than decrease. Further, major complications of minoxidil are rare, but possible, and patients who suffer from heart disease or hypertension cannot utilize this product without medical supervision.

The other approved product to treat alopecia is Propecia®, or finasteride. Propecia® originally was used to treat prostate enlargement by inhibiting the 5-alpha reductase enzyme. Men undergoing that treatment experienced an increase in hair growth while receiving finasteride. It is believed that the inhibition of the 5-alpha reductase enzyme may increase hair follicle growth or prevent future hair follicle loss. However, pregnant or nursing women may not use finasteride because the product is teratogenic, and can harm the human fetus. Due to such a serious health risk, Propecia® has been limited to use within male patient populations only, leaving a majority of female alopecia sufferers to seek alternative treatment options.

Because of the downfalls of currently approved drug therapies for the treatment and prevention of human alopecia conditions, cosmetic treatments have been developed as well. One cosmetic treatment, as noted within U.S. Pat. No. 4,999,187 to Vernon, discloses a hair and scalp treatment composition that comprises 60% by weight or more of petrolatum in combination with 5% by weight or more sulfur, 0.5% by weight or more of 1,2,3-propanetriol, and the remaining 0.5 to 10% of the composition comprised of an oil, such as coconut oil. The composition is said to treat the hair and scalp to effectively prevent dandruff in the hair while conditioning and causing the hair to grow in areas of the scalp where it had previously ceased to grow. However, the '187 patent does not disclose the use of its composition for a variety of alopecia conditions such as alopecia areata. Rather, the '187 patent merely addresses the conditioning of the hair and scalp.

Another cosmetic treatment involves implanting synthetic or artificial hair into hair follicle root bulbs of the scalp, or implanting expandable balloon structures under the scalp, to stimulate natural hair growth. However, it has been found that artificial hair implant methods are almost always unsuccessful. Such implants often become infected, leading to increased patient health risk and further natural hair follicle loss. In response to the failure of artificial hair transplants, other implant treatments utilizing human hair have been developed. Of human transplants available, four invasive surgical methods are currently preferred within the medical community.

The first of those surgical methods includes hair grafts, in which a graft of a small area of hair bearing scalp is moved from one area of the head to another. Alopecia or bald areas are replaced with hair bearing scalp tissue grafts to allow for development of new, natural hair in the transplanted area. However, when such a graft is moved from one area of the scalp to another area, it loses its blood supply, and must reestablish a new one. If a new blood supply cannot be reestablished upon placement of the graft or if infection occurs, this surgical method will fail, resulting in no new hair growth, only scarred tissue.

An alternative surgical method is the hair flap, in which a piece of scalp along with its blood supply is moved from one location on the head to another. This method generally is used only when large areas of hair bearing scalp need to be moved, and the procedure involves a lengthy recovery time. For those seeking a less invasive and shorter recovery time, excision or scalp reduction has been developed. Excision or scalp reduction involves removing the hairless scalp tissue areas and stretching the remaining non-hairless scalp to cover the defect. Here again, the patient is subjected to a surgical procedure with its inherent risks and complications.

The last cosmetic surgical treatment method for hair loss involves tissue expansion, in which small balloons are placed beneath the hair bearing scalp, and the balloons are then expanded slowly over several weeks to stretch the adjacent area of the scalp intended to be used to cover the defect. This method again, has surgical risks and complications including scarring, as well as a lengthier treatment and recovery period due to the length of time needed to stretch the existing scalp tissue and for the incisions to heal.

Although surgical cosmetic treatments for alopecia are available, many problems exist with such treatment options. The main problems specifically associated with all of these methods are the need for multiple operations, scarring when the scalp is moved or stretched, unexpected results, and development of numbness in the scalp following the surgical procedure. Further, the patient is subjected to the risks of surgery in general, as well as swelling, bruising, bleeding, and infection during the recovery process.

More than 40 U.S. and several hundred foreign patents have been issued for hair loss/alopecia treatment methods and compositions. Yet, no single agent or method of treatment has been found to universally work against all forms of hair loss. Thus, the treatment process is often one of trial and error, leaving the patient searching for the treatment that will produce the desired result for them.

There is a need in the prior art for a composition and method of treatment regimen for the treatment and prevention of a variety of human alopecia conditions that are non-invasive, can be used in male and female treatment populations without reproductive risk, and can prevent future hair follicle loss while stimulating new hair follicle growth. In addition, there is a need within the prior art for a composition and method of treatment regimen for the treatment and prevention of a variety of animal alopecia conditions to maintain and stimulate a healthy haircoat upon the animal's skin.

SUMMARY OF THE INVENTION

In commonly owned U.S. Provisional Patent Applications Nos. 60/190,286 and 60/194,322, a method is disclosed for treating or preventing human or animal alopecia conditions by cutting the hair, heat sealing the cut ends, and applying a heated oil composition of preferably at least about 50% coconut oil either before or after the cutting and sealing steps.

The present invention is a hand-held device which is novel and facilitates the heat-sealing step in the treatment described above. A handle supports a heating element, and a protective shroud encloses the heating element thereby shielding a patient from accidental contact with the high temperature heating element. An aperture in the shroud permits hair to enter the shroud where it is heat-sealed by the heating element. The aperture is of sufficient size to allow hair to enter, yet is designed to minimise the risk of the patient's skin contacting the hot components inside the shroud.

In another aspect of the invention a vacuum source is provided to draw fumes away form the proximity of the heating element of a hand-held heating device. This is effective in drawing away fumes created as hair is sealed by the heating element.

These and other features, advantages and objects of the present invention will be further understood and appreciated by those skilled in the art by reference to the following specification and claims. A more detailed description of the present invention shall be discussed further below.

BRIEF DESCRIPTION OF THE DRAWINGS

The present invention will now be described, by way of example, with reference to the accompanying drawings, in which:

FIG. 1 is a drawing of the hand piece of the invention illustrating much of the internal structure of the hand piece.

FIG. 3 is a perspective view of the hand piece.

DESCRIPTION OF THE PREFERRED EMBODIMENT

Figure 2:
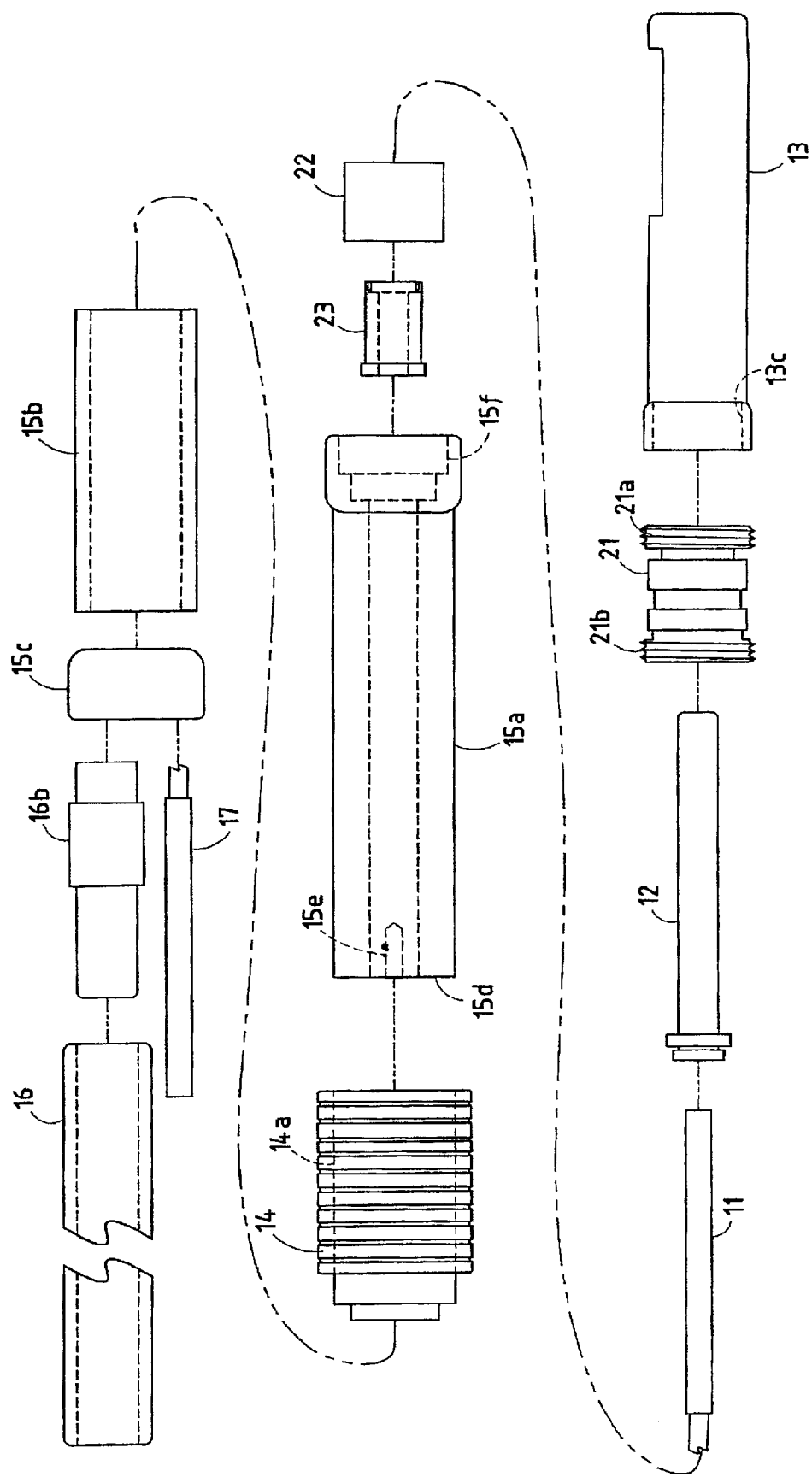
FIG. 2 is an exploded view of the hand piece.

In the preferred embodiment, the instrument includes a hand-held device having a heating element, a protective shroud, and a handle. The hand-held device is connected to a control unit that provides electrical power to the heating unit and to a vacuum source that draws fumes from the area around the heating element. The heating element is heated to a temperature of from about 400° F. to about 1,000° F. sufficient for fusing and sealing the cuticle, cortex, and medulla layers of a hair shaft. The instrument is preferably used after the hair has been cut and either before or after the oil treatment has been applied. The operator sets the heating element to a desired temperature, grips the handle of the hand-held device, and maneuvers the heating element to contact the target hair.

In the preferred embodiment, the heating element is enclosed inside a polished chrome plated copper sheath that is thermally coupled to the heating element. The sheath, not the heating element, then contacts the hair to perform the heat-sealing process.

When the hand-held device is in use, various fumes are produced including smoke. An air channel runs through the interior of the hand-held device from the butt of the handle to near the heating element. The butt of the hand-held device is connected to the vacuum source thereby drawing fumes from the proximity of the heating element, through the handle, and through an air hose to the vacuum source. As part of the vacuum process, the fumes and air are filtered.

Turning to FIG. 1, the hand-held device 10 of the invention is illustrated in a semi-transparent depiction such that many of the elements are shown assembled together. Hand-held device 10 includes heating element 11, sheath 12, shroud 13, shroud aperture 13A, guard 14, and handle 15. Also illustrated are air hose 16 and electrical cable 17 that connect to the butt 10A of hand-held device 10.

Heating element 11 is a 100 watt resistive type heating element well known to those skilled in the art. The preferred embodiment operates on 24 volts AC and includes a type K thermocouple type heat sensor built into heating element 11. Four wires exit the base of the heating element; two wires for providing electrical power and two wires for the temperature signal from the thermocouple. In the prototype, heating element is approximately 3/8 inch in diameter and 5 5/16 inch in length.

Heating element 11 is secured to hand-held device 10 by a hollow cylindrical copper sheath 12. Heating element 11 is positioned inside of sheath 12 which is then threading onto the retainer (not shown) component of hand-held device 10 as illustrated below. Sheath 12 has a polished chrome finish and is thermally coupled to heating element 11 via a thermally conductive paste filling the gap between heating element 11 and the interior of sheath 12. Other surfaces may also be used for sheath 12. For example, it is envisioned that polished metal surfaces, fluoropolymer resins (i.e. TEFLON®), cooking surfaces, and the like will also work well. In the prototype, sheath 12 is approximately 5/8 inches in diameter and 6 1/4 inches in length.

Sheath 12 and heating element 11 are both positioned inside of shroud 13. Shroud 13 is a substantially hollow cylindrical shaped protective device intended to shield a patient from the high temperatures of heating element 11 and sheath 12. These elements may reach a temperature of about 1,000° F. and can easily burn a patient. Shroud 13 is made of aluminium with a porcelain power coating. A heating element cavity 13B includes the hollow area inside of shroud 13 and houses sheath 12 and heating element 11. Hair-inlet aperture 13A is located on the side of shroud 13 and is sized and shaped to allow hair to enter the heating element cavity 13B while preventing a firm surface (e.g. a patient's scalp) from contacting the high temperature sheath 12 or heating element 11. In alternate embodiments, such as shown in FIG. 3, hair-inlet aperture 13A is comprised of multiple apertures. Shroud 13 threads onto other components of the hand-held device 10 as discussed below.

Adjacent to the base of shroud 13 is guard 14. Guard 14 is another safety/protective feature of the invention that protects the hand of an operator from shroud 13. Even though shroud 13 is generally cooler than heating element 11, it may still be hot enough to burn or to be uncomfortable. Guard 14 is made of high temperature plastic such as garolite and insulates the operator from shroud 13. Guard 14 is secured to handle 15 and has a large guard cavity 14A which allows it to extend over the base of shroud 13 without touching shroud 13.

Continuing along FIG. 1, an operator grips the hand-held device 10 via handle 15. Handle 15 includes a plastic frame 15A (see FIG. 2) surrounded by a neoprene rubber cover 15B and an end cap 15C. The plastic frame 15A is substantially hollow and provides a channel for the electrical wires 17 that connect to the heating element 11 and for airflow from the area around heating element 11 to air hose 16. Both the electrical wires 17 and the air hose 16 connect to handle via end cap 15C which threads onto frame 15A.

Air hose 16 is preferably made of a high quality plastic that is able to withstand elevated temperatures. It was found during testing, that a small diameter air hose would become overheated as hot air from the heater element 11 was drawn through the hose. The solution was to increase the diameter of air hose 16 for increased airflow and to use heat tolerant materials. Air hose 16 attaches to hand-held device 10 via coupling 16A.

Electric wires 17 are preferably a high quality electric cable having a braided wire mesh covering the wires. The wire mesh is coated in plastic or similar material and yields a preferred electric cable for the invention.

Referring to FIG. 2 there is shown an exploded view of the hand-held device 10 that shows the components in more detail. Beginning at the bottom of the drawing, shroud 13 threads onto adapter 21 via shroud threads 13C and front adapter threads 21A. This arrangement allows a user to easily remove and clean device 10 as needed. Heating element 11 is inserted into sheath 12, and sheath 12 threads into retainer 23. Ceramic bobbin 22 is clamped between sheath 12 and retainer 23 when sheath 12 and retainer 23 are threaded together. Bobbin 22 has a hole through its center for receiving retainer 23. However, the hole is smaller diameter than the ridge on the base of sheath 12 and bobbin 22 is thereby secured to retainer 23 and sheath 12. Bobbin 22 also provides additional channels for wire 17 from heating element 11 and for airflow drawn from the area proximate to heating element 11. Bobbin 22 serves to insulate the other components from heating element 11.

When sheath 12 is secured to retainer 23, a rigid unit is created comprising the retainer 23, bobbin 22, heating element 11, and sheath 12. This unit is inserted into adapter 21 with sheath 12 extending into the heating element cavity 13B of shroud 13. Adapter 21 is preferably made of aluminium, while retainer 23 is made of steel and bobbin 22 is ceramic.

Continuing with the assembly of the hand-held device 10, the handle frame 15A is treaded onto adapter 21 via rear adapter threads 21B and front frame threads 15F. This secures all of the prior assembled components into a rigid unit. Guard 14 is slid onto the rear 15D of frame 15A and slide forward along handle frame 15A until it stops and guard cavity 14A substantially surrounds the retainer 23, bobbin 22, and the base of shroud 13. Plastic handle frame 15A can still get warm from the hot air drawn through its hollow interior; therefore neoprene rubber cover 15B is slid onto handle frame 15A to provide insulation and a good gripping surface. End cap 15C is then secured to handle frame 15A via two screws threaded into screw holes 15E. The rear of end cap 15C forms the butt 10A of and hand-held device 10. Air hose 16 connects to end cap 15C via connector 16A and electrical wires 17 enter end cap 15C.

Turning to FIG. 3 there is shown a perspective view of hand-held device 10 that also illustrates some alternate embodiments of the invention. An embodiment having multiple hair inlet apertures 13A is shown. Multiple hair inlet apertures may provide better protection against burn injury to a patient; however, it restricts access of hair to the heating element. Another embodiment equips shroud 13 with teeth 13C that function as a comb and are useful in some applications.

Figure 4:
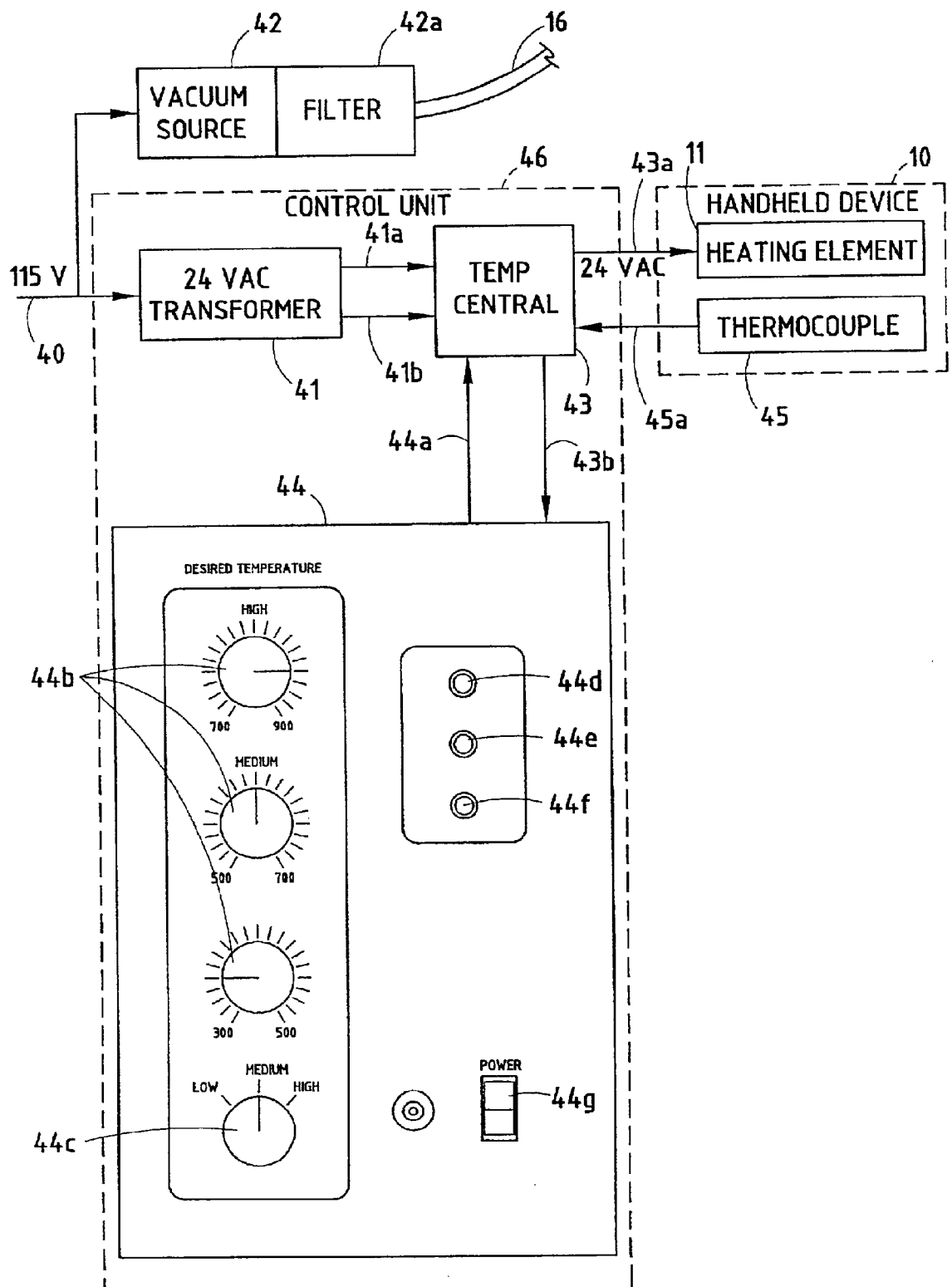
FIG. 4 is a block diagram of the invention.

Looking now to FIG. 4, a block diagram of the apparatus is shown. A power source (not shown) provides 115VAC power 40 to medical isolation transformer 41 and vacuum source 42. Medical transformers are often required to power medical devices and are well known in the art. Although it is not required for the operation of the invention, the medical transformer 41 is included to insure compliance with generally accepted standards. Medical transformer 41 provides an isolated 24VAC-power signal 41A to temperature control 43. Power signal 41A is used by temperature control 43 to power heating element 11.

Temperature control 43 controls the temperature of heating element 11. The prototype unit uses a conventional temperature controller such as the PC Programmable Thermocouple Sensing Temperature Controller, model number 5C7-461, manufactured by Oven Industries of Mechanicsburg, Penn. The Operating Manual for the controller is herein incorporated by reference. Those skilled in the art understand that many such temperature control circuits and devices are available and known. The 115VAC signal 41B provides power to temperature control 43.

The operation of temperature control 43 is straightforward. An operator enters a desired temperature via user interface 44. User interface 44 generates a temperature command signal 44A representative of the desired temperature and communicates command signal 44A to temperature control 43. The current temperature of heating element 11 is unknown, so temperature signal 45A is communicated from temperature sensor (e.g. thermocouple) 45. Temperature signal 45A provides the feedback data used by temperature control 43 to accurately control the temperature of heating element 11.

In the preferred embodiment, command signal 44A is simply resistance from one of three potentiometers or variable resisters 44B in user interface 44. Each potentiometer 44B has a different resistance range and therefore each potentiometer 44B generates a different temperature command signal. The desired potentiometer is selected using a three-way switch 44C.

Alternate embodiments include, for example, implementing a digital user interface which would generate a digital command signal 44A instead of an analog resistance type signal. Also, thermocouple 45 can be any type of suitable temperature sensor.

Temperature control 43 controls electrical power signal 43A to heating element 11 as a function of command signal 44A from user interface 44 and feedback temperature signal 45A from thermocouple 45. Temperature control 43 communicates a status signal 43B back to user interface 44 which activates one of three lights 44D, 44E and 44F thereby indicating if the measured temperature is above, at, or below the commanded temperature. Lamp 44D is activated if the actual temperature is above the commanded temperature. Similarly, lamp 44F is activated if the actual temperature is below the commanded temperature. If the actual temperature is within a predetermined range specified by the command signal 44A, then lamp 44E is activated. Power switch 44G switches power signal 40 on and off to components of control unit 46.

Temperature control 43 controls the temperature of heating element 11 to between about 400° F. to about 1,000° F., preferably between about 600° F. to about 1,000° F., and more preferably between about 800° F. to about 1,000° F.

Vacuum source 42 is any device capable of drawing a sufficient volume of air through hand-held device 10 to draw fumes from around heating element 11. Vacuum sources are well known in the art. Vacuum source 42 includes a filter 42A for filtering the fumes and particles drawn in by the vacuum source 42. It is preferred to use a high efficiency HEPA filters because of their excellent filtering characteristics. However, other filters may be adequate under certain conditions.

Figure 5:
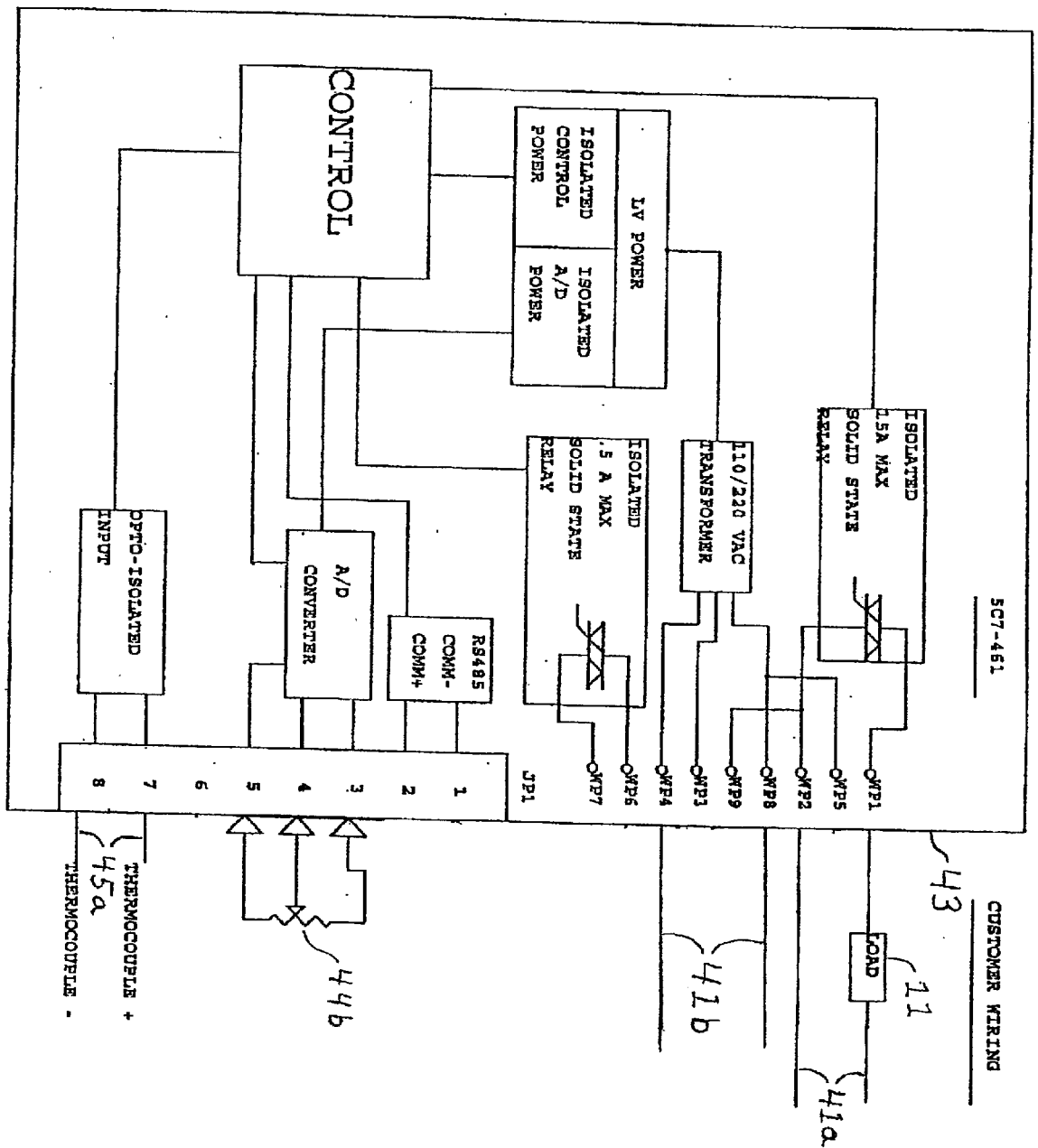
FIG. 5 is a block diagram of a temperature controller.

A block diagram of temperature control 43, model number 5C7-461 manufactured by Oven Industries, is shown in FIG. 5 connected to other elements of the apparatus. Load or heating element 11 is shown with one lead connected to pin WP1 and a second lead connected to 24 VAC power signal 41A. The circuit is completed when power signal 41A is connected to pin WP2. Control 43 controls the power to heating element 11 via a relay internal to control 43. Power is provided to temperature control 43 via 115 volts alternating current (VAC) signal 41B which connects to pins WP8 and WP4. Potentiometers or variable resisters 44*b* connect to pins 3, 4, and 5 of connector JP1. The temperature signal 45A from thermocouple 45 connects to pins 7 and 8 of connector JP1. Temperature controller 43 can be connected to a personal computer or the like in order for a user to set or modify parameters. For example, a user can program the desired control algorithm parameters such as proportional (P), integral (I), and derivative (D), or various combinations of P, I, and D. In the alternative, an ON/OFF mode may be selected with hysteresis.

The hair treatment instrument of the present invention performs the heat sealing process for a method of treating alopecia. The instrument effectively heat-seals the hair of a patient and disposes of fumes generated from the process.

It will be understood by those who practice the invention and those skilled in the art, that various modifications and improvements may be made to the invention without departing from the spirit of the disclosed concept. The scope of protection afforded is to be determined by the claims and by the breadth of interpretation allowed by law.

What is claimed is:

1. A heat-sealing instrument comprising:
    a shroud having,
        a hair inlet aperture, and,
        a heating-element cavity;
    a non-transparent a sheath positioned in said heating-element cavity;
    a heating element positioned in said heating-element cavity, wherein said heating element is positioned within said sheath and is thermally coupled to said sheath; and,
    a handle supporting said shroud.

2. The heat-sealing instrument according to claim 1 wherein said hearing element is heated to between about 400° F. to about 1,000° F.

3. The heat-sealing instrument according to claim 2 wherein said heating element is heated to between about 600° F. to about 1,000° F.

4. The heat-sealing instrument according to claim 3 wherein said heating element is heated to between about 800° F. to about 1,000° F.

5. The heat-sealing instrument according to claim 1 further comprising a thermally conductive paste positioned between said heating element and said sheath.

6. The heat-sealing instrument according to claim 5 wherein said sheath includes a polished surface.

7. The heat-sealing instrument according to claim 1 further comprising a vacuum source drawing fumes from the proximity of said heating element.

8. The heat-sealing instrument according to claim 7 wherein said vacuum source includes a hose connected to said handle.

9. The heat-sealing instrument according to claim 8 wherein said vacuum source draws said fumes through the interior of said handle.

10. The heat-sealing instrument according to claim 7 further comprising a filter, said filter filtering said fumes drawn from the proximity of said heating element.

11. The heat-sealing instrument according to claim 1 further comprising a temperature control unit in communication with said heating element.

12. The heat-sealing instrument according to claim 11 further comprising a temperature sensor in communication with said temperature control unit, said sensor detecting a temperature proximate to said heating element and generating a temperature signal indicative of the temperature of said heating element.

13. The heat-sealing instrument according to claim 12 wherein said temperature sensor is a thermocouple.

14. The heat-sealing instrument according to claim 11 further comprising a user interface in communication with said temperature control unit and wherein said control unit is responsive to temperature commands from said user interface.

15. The heat-sealing instrument according to claim 1 wherein said shroud includes teeth.

16. An apparatus for the treatment of alopecia comprising:
    a shroud having a heating-element cavity, wherein said shroud includes a hair inlet aperture;
    a non-transparent a sheath positioned in said heating-element cavity;
    a heating element positioned in said heating-element cavity, wherein said heating element is positioned within said sheath and is thermally coupled to said sheath;
    a handle supporting said heating element; and, a vacuum source drawing in fumes from the proximity of said heating element.

17. The apparatus for the treatment of alopecia according to claim 16 wherein said heating element is heated to between about 400° F. to about 1,000° F.

18. The apparatus for the treatment of alopecia according to claim 17 wherein said heating element is heated to between about 600° F. to about 1,000° F.

19. The apparatus for the treatment of alopecia according to claim 18 wherein said heating element is heated to between about 800° F. to about 1,000° F.

20. The apparatus for the treatment of alopecia according to claim 16 wherein said vacuum source includes an air hose connected to said handle, whereby said fumes are drawn in by said vacuum source.

21. The apparatus for the treatment of alopecia according to claim 20 wherein said air hose draws said fumes through the interior of said handle.

22. The apparatus for the treatment of alopecia according to claim 16 further comprising an air filter filtering said fumes drawn in by said vacuum.

23. The apparatus for the treatment of alopecia according to claim 16 further comprising, a temperature sensor generating a temperature signal indicative of the temperature of said heating element; and, a temperature control, in communication with said temperature sensor and controlling the temperature of said heating element as a function of said temperature signal.

24. The apparatus for the treatment of alopecia according to claim 23 further comprising a user interface in communication with said temperature control and wherein said temperature control is responsive to temperature commands from said user interface.

25. The apparatus for the treatment of alopecia according to claim 16 further comprising a thermally conductive paste positioned between said heating element and said sheath.

* * * * *